United States Patent [19]

O'Young et al.

[11] Patent Number: 4,774,220

[45] Date of Patent: Sep. 27, 1988

[54] LITHIUM-DOPED GAMMA-ALUMINA SUPPORTED COBALT-MOLYBDENUM CATALYST

[75] Inventors: Chi-Lin O'Young, Brewster; Guillermo Prada-Silva, Wappingers Falls, both of N.Y.

[73] Assignee: Texaco, Inc., White Plains, N.Y.

[21] Appl. No.: 20,835

[22] Filed: Mar. 2, 1987

[51] Int. Cl.[4] .......................... B01J 21/04; B01J 23/78; B01J 23/88
[52] U.S. Cl. .................................................. 502/314
[58] Field of Search ................................ 502/314, 317

[56] References Cited

U.S. PATENT DOCUMENTS 4,661,525  4/1987  Grazioso et al. ............... 502/206 X Primary Examiner—W. J. Shine
Attorney, Agent, or Firm—Robert A. Kulason; Robert B. Burns; James J. O'Loughlin

[57] ABSTRACT

A lithium-doped gamma-alumina supported cobalt-molybdenum catalyst and a process for converting synthesis gas to a mixture of lower aliphatic alcohols is provided.

4 Claims, No Drawings

LITHIUM-DOPED GAMMA-ALUMINA SUPPORTED COBALT-MOLYBDENUM CATALYST

BACKGROUND OF THE INVENTION

Field of the Invention

This invention relates to a novel lithium-doped gamma-alumina supported cobalt-molybdenum catalyst and to a process for converting synthesis gas to a mixture of lower aliphatic alcohols characterized by containing a substantial proportion of alcohols having from 2 to 6 carbon atoms.

Lower aliphatic alcohols have been proposed as fuel extenders for gasoline for fueling internal combustion engines. Certain mixtures of lower aliphatic alcohols for use in motor fuels have the EPA approval and are currently being marketed in the United States. The lower aliphatic alcohols can be produced from a domestically available non-petroleum source, and their use in fuels serves to lessen dependence on imported crude oil or petroleum products.

Hydrogen and carbon monoxide, or a synthesis gas mixture of same, can be reacted to form lower aliphatic alcohols. A synthesis gas feedstream can be produced from non-petroleum sources, such as coal, biomass or other hydrocarbonaceous materials. The synthesis gas mixture can be produced in a partial oxidation reaction of the hydrocarbonaceous material as, for example, in a coal gasification process.

Numerous catalytic processes have been studied in attempts to provide a viable process for the production of aliphatic alcohols from synthesis gas or from a mixture of hydrogen and carbon monoxide. Earlier developments were primarily directed to the production of methanol. In contrast to this, the present process is directed to a method for producing an alcohol mixture containing a substantial amount of aliphatic alcohols having from 2 to 6 carbon atoms.

A major problem with the synthesis gas to alcohol conversion process is the occurrence of competing reactions constantly taking place on the surface of the catalyst. Thus, even when the desired product is formed on the catalyst, some of this product may undergo further reactions with adverse effects on the yield of the desired product. It is evident that if some means could be provided for reducing or minimizing competing reactions on the catalyst surface, then improved yields of the desired product might be obtained.

Disclosure Statement

U.S. Pat. No. 3,345,427 discloses a dehydrogenation catalyst and process in which the catalyst consists of nickel, molybdenum and alkaline metal oxides on an alumina support.

U.S. Pat. No. 4,096,164 discloses a process for reacting hydrogen and carbon monoxide in the presence of a solid catalyst comprising rhodium with molybdenum or tungsten to produce 2 carbon-atom oxygenated hydrocarbons in which ethanol is the major compenent.

EPA No. 119609 discloses a process for producing alcohols from synthesis gas using a catalyst containing molybdenum with tungsten, rhenium and an alkaline metal.

U.S. Pat. No. 4,607,055 discloses a process for converting synthesis gas to a mixture of aliphatic alcohols in the presence of a catalyst comprising molybdenum, a metal from the group consisting of cobalt, iron and nickel, and silver, with an alkali metal promotor from the class consisting of potassium, cesium and rubidium.

Co-assigned applications Ser. No. 728,636 filed Apr. 29, 1985, now U.S. Pat. No. 4,661,525, is directed to a process for converting synthesis gas to a mixture of lower aliphatic alcohols in the presence of a catalyst comprising molybdenum and a metal selected from the group consisting of cobalt, iron and nickel which has been promoted by an alkali metal selected from the group consisting of potassium, cesium and rubidium.

The disclosures of U.S. Pat. No. 4,607,055, EPA Pat. No. 119609 and application Ser. No. 728,636, now U.S. Pat. No. 4,661,525, are incorporated herein by reference.

Summary of the Invention

The novel catalyst composition of the invention comprises a lithium-doped, gamma-alumina supported cobalt-molybdenum catalyst comprising from about 3 to 25 weight percent of molybdenum calculated as $MoO_3$, from about 0.3 to 5 wt. % of cobalt calculated as $CoO$ and from about 2 to 12 wt. % of an alkali metal selected from the class consisting of potassium, cesium and rubidium and the balance said support, said support comprising gamma-alumina containing from about 0.1 to 1.0 wt. % of lithium incorporated in said gamma-alumina.

The novel process of the invention comprises the reaction of carbon monoxide and hydrogen in the presence of the prescribed catalyst composition to produce a mixture of lower aliphatic alcohols characterized by containing a substantial amount of aliphatic alcohols having from 2 to 6 carbon atoms.

Detailed Embodiments of the Invention

In accordance with this invention, the novel catalyst composition of the invention comprises in part a specific gamma alumina support material which promotes an increase in the ratio of higher alcohols to methanol in the process of the invention. The base or support used in the catalyst preparation comprises gamma alumina which has been modified by incorporating lithium into the interstices of the gamma alumina. More particularly from about 0.1 to 1.0 weight percent of lithium is incorporated into the gamma-alumina support. This is accomplished by treating the gamma-alumina support with an aqueous solution of a lithium salt using the incipient witness impregnation technique. The treated support is then dried and subsequently calcined in air at a temperature that is high enough to effect solid state diffusion of the lithium ions into the spinal structure of gamma alumina. In general, the calcination temperature will be in the order of about 600° C. or higher.

The prescribed lithium-doped gamma-alumina is then contacted with a source of molybdenum generally in the form of a soluble salt and then with a source of cobalt also in the form of a soluble salt to impregnate the doped gamma alumina support with molybdenum and cobalt. The impregnation of the carrier can be done simultaneously or sequentially. The impregnated carrier is then dried and calcined according to known procedures.

Subsequent to the calcination of the heavy metals onto the lithium modified gamma alumina, the catalyst is contacted with an alkali metal from the class of potassium, cesium or rubidium. The alkali metal is incorporated generally using the incipient wetness procedure following which the catalyst is subjected to reduction with hydrogen gas generally by heating the catalyst at a temperature between about 300° and 500° C. for an extended period, usually from 2 to 8 hours. In general, the lithium-doped, gamma-alumina supported cobalt-molybdenum catalyst will comprise from about 3 to 25 wt. % of molybdenum, calculated as $MoO_3$, from about 0.3 to 5 wt. pecent of cobalt calculated at CoO and from about 2 to about 12 wt. percent of an alkali metal selected from the class consisting of potassium, cesium and rubidium and the balance said lithium-doped support comprising gamma-alumina containing from about 0.1 to 1.0 wt. % of lithium incorporated or infused into said gamma-alumina.

A preferred catalyst composition comprises from about 5 to 10 wt. percent of molybdenum, from about 1.5 to 3 wt. percent of cobalt and from about 5 to 10 wt. percent of said alkali metal with the balance said lithium-doped gamma-alumina containing from about 0.2 to 0.3 wt. percent of lithium.

A still more preferred catalyst will contain from about 5.5 to 7 weight percent of molybdenum, and potassium in an amount ranging from about 7 to 8 wt. percent calculated as potassium metal.

The carbon monoxide and hydrogen employed to form the lower aliphatic alcohols in this process can be provided from any available source. One particularly useful source is synthesis gas produced in the gasification of hydrocarbonaceous materials, such as coals and biomass. An effective gasification process is described in U.S. Pat. No. 3,544,291 wherein a hydrocarbonaceous fuel is partially oxidized with a free oxygen-containing gas in a gas generator. In general, the mole ratio of hydrogen to carbon monoxide employed in this process should range from about 0.1 to 50 moles of hydrogen per mole of carbon monoxide with the preferred ratio being from about 0.5 to 20 moles of hydrogen per mole of carbon monoxide.

The reaction conditions for effecting the conversion of the carbon monoxide-hydrogen feed into lower aliphatic alcohols employing the prescribed catalyst of the invention includes a reaction temperature ranging from about 240° to about 400° C. with a more preferred temperature range being from about 300° to about 360° C., and the most preferred temperature range being from about 330° to 350° C. The effective pressure range for this process is from about $3.4 \times 10^6$ Pa (500 psi) to about $2.4 \times 10^7$ Pa (3500 psi). The preferred pressure range is from about $5.1 \times 10^6$ Pa (750 psi) to about $1.7 \times 10^7$ Pa (2500 psi).

The space velocity employed to effect the conversion of carbon monoxide and hydrogen over the prescribed catalyst to the aliphatic alcohols is important. In general, the space velocity, that is the volume of gas passed through a given volume of catalyst per hour expressed as $GHSV(hr^{-1})$, must be at least 1000. A preferred range is from about 5000 to about 50,000. A highly effective process is realized when the space velocity employed ranges from about 10,000 to about 30,000. Under preferred conditions the ratio of weight percent of $C_2$–$C_6$ alcohols to weight percent methanol will substantially exceed 1, and can range from 1.25 to 2 or above.

The practice of this invention is described in the following Example. In this Example, the reaction was carried out in a 0.5 liter stainless steel Berty type recirculating gradientless reactor from Autoclave Engineers. The product emerging from the stainless steel reactor was then sent through a condenser which liquefied the alcohol and water products. The resulting liquid was analyzed by gas chromatography. The weight ratio of $C_2$–$C_6$ alcohol production to methanol production (R) is given as well as the alcohol production expressed as grams of alcohol per gram of catalyst per hour (g/g-hr).

Commercially available gamma alumina was employed as the support material in the preparation of the comparison cobalt molybdenum catalyst and the catalyst of this invention. The catalyst of this invention employed a lithium impregnated or lithium doped alumina support which was prepared by incipient wetness impregnation of the gamma alumina with an aqueous solution of lithium nitrate. The support was dried at 120° C. for 2 hours and calcined at about 600° C. for 4 hours, to effect diffusion of the lithium ions into the gamma alumina.

The molybdenum component was then added onto the support by incipient wetness impregnation with an aqueous solution of ammonium heptamolybdate. The molybdenum impregnated support was dried followed by calcination in air at 500° C. for 4 hours.

Cobalt and potassium were then added by coimpregnation with an aqueous solution of their salts. The resulting catalyst was then dried and calcined in air at 400° C. for 4 hours.

A mixture of carbon monoxide and hydrogen consisting of about 2 moles of hydrogen per mole of carbon monoxide was contacted with the catalyst in a reactor in which reaction temperature was maintained between about 338° to 343° C. using a gas flow rate of about 15,000 volumes of the gaseous reactants per volume of catalyst per hour.

The results of these tests are set forth in Table I below. In the Table R represents the wt. ratio of higher aliphatic alcohols that is alcohols having from $C_2$ to $C_6$ carbon atoms to the wt. ratio of methanol. The results and reaction conditions are set forth in Table I below.

TABLE I

| K/Co/Mo/on Lithium-Infused $Al_2O_3$ CATALYSTS | | | | | | |
|---|---|---|---|---|---|---|
| Cat Code No. | Run 1 | Run 2 | Run 3 | Run 4 | Run 5 | Run 6 |
| Composition | | | | | | |
| Mo | 6.58 | 5.97 | 5.73 | 6.02 | 6.67 | 5.71 |
| Co | 1.02 | 1.59 | 1.58 | 1.51 | 2.45 | 2.39 |
| K | 7.57 | 7.65 | 7.80 | 7.16 | 7.22 | 7.85 |
| Li | 0 | 0.03 | 0.12 | 0.24 | 0 | 0.22 |
| R | 1.00 | 1.00 | 1.05 | 1.41 | 1.20 | 2.08 |
| Alcohol Selectivity (%, $CO_2$ free) | 63 | 56 | 58 | 59 | 45 | 45 |
| Alcohol Activity (g/g-hr) | 0.21 | 0.18 | 0.19 | 0.21 | 0.27 | 0.26 |
| Reactor Temp. (°C.) | 340 | 340 | 340 | 340 | 343 | 338 |

The foregoing runs demonstrate the significant effect that a lithium doped gamma alumina has toward directing the course of the reaction toward producing higher amounts of higher aliphatic alcohols. Comparison Runs 5 and 6 is a good illustration of this directed reaction. Run 5 which contain no lithium in the gamma alumina produce a ratio of higher alcohols to methanol of 1.2. When 0.22 wt. percent of lithium was incorporated into the gamma alumina base or support material, the wt. ratio of higher aliphatic alcohols to methanol was found to be 2.08.

The foregoing data demonstrates that the process for the production of lower aliphatic alcohols from a mixture of carbon monoxide and hydrogen within the critical parameters for the prescribed catalyst supported on a lithium modified or doped gamma alumina is effective for producing a substantial improvement in the production of $C_2$-$C_6$ aliphatic alcohols in relation to the production of methanol.

We claim:

1. A lithium-doped gamma-alumina supported cobalt-molybdenum catalyst comprising from about 3 to 25 wt. percent of molybdenum calculated as $MoO_3$, from about 0.3 to 5 wt. percent of cobalt, calculated as CoO and from about 2 to 12 wt. percent of an alkali metal selected from the class consisting of potassium, cesium and rubidium, and the balance said support, said support comprising gamma-alumina containing from about 0.1 to 1.0 wt. percent of lithium diffused in said gamma-alumina at a temperature of about 600° F. or above.

2. A lithium-doped gamma-alumina supported catalyst according to claim 1 containing from about 5 to 10 wt. percent of molybdenum, from about 1.5 to 3 wt. percent of cobalt from about 5 to 10 wt. percent of said alkali metal and from about 0.2 to 0.3 wt. percent of lithium in said gamma-alumina.

3. A lithium-doped gamma-alumina supported cobalt-molybdenum catalyst according to claim 1 in which said alkali metal promoter is potassium at a concentration ranging from about 7 to 8 wt. percent.

4. The catalyst composition according to claim 1 in which said lithium metal is diffused in said gamma-alumina at a temperature of about 600° F. or above

* * * * *